United States Patent
Regan et al.

(10) Patent No.: US 6,395,878 B1
(45) Date of Patent: May 28, 2002

(54) NUCLEIC ACID ENCODING A HUMAN EP PROSTAGLANDIN RECEPTOR

(75) Inventors: John W. Regan, Tucson, AZ (US); Daniel W. Gil, Corona del Mar; David F. Woodward, Lake Forest, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/267,423

(22) Filed: Mar. 12, 1999

Related U.S. Application Data

(60) Continuation-in-part of application No. 09/019,393, filed on Feb. 5, 1998, now abandoned, which is a division of application No. 08/239,431, filed on May 5, 1994, now Pat. No. 5,716,835.

(51) Int. Cl.$^7$ .......................... C07K 1/00; C07K 14/00; C07K 17/00; A61K 38/00
(52) U.S. Cl. ........................ 530/350; 530/300; 530/403
(58) Field of Search ............................... 530/300, 350, 530/403

(56) References Cited

U.S. PATENT DOCUMENTS

| | | | |
|---|---|---|---|
| 5,516,652 A | * | 5/1996 | Abramovitz et al. |
| 5,795,752 A | | 8/1998 | Smith |
| 5,871,960 A | * | 2/1999 | Smith et al. |
| 6,051,398 A | | 4/2000 | Smith et al. |

OTHER PUBLICATIONS

Rudinger J. et al. Characteristics of the amino acids as components of a peptide hormone sequence. in Peptide Hormones. pp. 1–7. Edited by Parsons, JA; Mill Hill, London, 1976.*
Honda et al. Cloning and expression of a cDNA for mouse prostaglandin E receptor EP2 subtype. J. Biol. Chem. 268:7759–7762, 1993.*
An, S. et al., Cloning and expression of the EP2 subtype of human receptors for prostaglandin E2. Biochemical and Biophysical Research Communications 197:263–270 (1993).
Coleman, R.A. , Eicosanoids and other bioactive lipids in cancer, inflammation and radiation injury. Nigam, S. et al. eds. 135–151 (1991).
Coleman, R.A. et al., A novel inhibitory prostanoid recptor in piglet saphenous vein. Prostaglandins 47:151–168 (1994).
Dong, Y.J. et al., Prostagladin E receptor subtypes in smooth muscle: agonist activities of stable prostacyclin analogues. Br. J. Pharmacol. 87:97–107 (1986).
Funk, C.D. et al., Cloning and expression of a cDNA for the human prostaglandin E receptor $EP_1$ Subtype. J. Biol. Chem. 268(35):26767–26772 (1993).
Gardiner, P.J., Characterization of prostanoid relaxant/inhibitory receptors using a highly selective agonist, TR4979. Br. J. Pharmacol. 87:45–56 (1986).

Giles, H. More selective ligands at eiconsanoid receptor subtypes improve prospects in inflammatory and cardiovascular research. Trends Pharm. Sci. 11:301–304 (1990).
Hébert, R.L. et al., $PGE_2$ inhibits AVP–induced water flow in cortical collecting ducts by protein kinase C activation. Am. J. Physiol. 259:F318–F325 (1990).
Hirata, M. et al., Cloning and expression of cDNA for a human thromboxane $A_2$ receptor. Nature 349:617–620 (1991).
Honda, A. et al., Cloning and expression of a cDNA for mouse prostaglandin E receptor $EP_2$ subtype. J. Biol. Chem. 268(11):7759–7762 (1993).
Humbles, A.A. et al., Phamacological characterisation of the protanoid receptors in the rabbit isolated ear artery. Br. J. Pharmcol. 108:74P (1993).
Milne, S.A. et al., Further investigation of prostanoid EP receptors in rabbit jugular and pig saphenous veins. Br. J. Pharmacol. III:79P (1994).
Nials, A.T. et al., AH13205, a selective prostanoid $EP_2$–receptor agonist. Cardiovascular Drug Reviews 11(2):165–179 (1993).
Regan, J.W. et al., Molecular cloning and expression of human $EP_3$ receptors: evidence of three variants iwth differing carboxyl termini. Br. J. Pharmacol. 112:377–385 (1994).
Senior, J. et al., In vitro characterization of prostanoid EP–receptors in the non–pregnant human myometreium. Br. J. Pharmacol. 102:747–753 (1991).
Smith, W.L., Prostanoid biosynthesis and mechanisms of action. Am. J. Physiol. 263:F181–F191 (1992).
Sonnenburg, W.K. and Smith, W.L., Regulation of cyclic AMP metabolism in rabbit cortical collecting tubule cells by prostaglandins. J. Biol. Chem. 263(13):6155–6160 (1988).
Sugimoto, Y. et al., Cloning and expression of a cDNA for mouse prostaglandin E receptor $EP_3$ Subtype. J. Biol. Che m. 267(10):6463–6466 (1992).
Woodward, D.F. et al., Identification of 19 (R)–OH prostaglandin $E_2$ as a selective prostanoid $EP_2$–receptor agonist. Prostaglandins 46:371–383 (1993).
Yeardley, H.L. et al., The effects of spasmolytic and spasmogenic prostanoids on cyclic amp levels in human myometrium from pregnant donors. Br. J. Pharmacol. Proc. Suppl. 108:174p (1992).

(List continued on next page.)

*Primary Examiner*—Gary L. Kunz
*Assistant Examiner*—Robert S. Landsman
(74) *Attorney, Agent, or Firm*—Carlos A. Fisher; Robert J. Baran; Martin A. Voet

(57) ABSTRACT

A gene encoding the HP4 human prostaglandin receptor is disclosed. The protein encoded by this gene exhibits significant sequence identity with other prostaglandin receptors. The HP4 receptor, when expressed in eukaryotic cells, is capable of binding prostaglandins and their analogs and stimulating adenylate cyclase activity in response to prostaglandins. Also disclosed are antisense agents able to decrease or prevent translation of a human HP4 prostaglandin receptor.

17 Claims, 2 Drawing Sheets

OTHER PUBLICATIONS

Bastein, Lison et al.; The Journal of Biological Chemistry; vol. 269, No. 16, Apr. 22, 1994, pp. 11873–11877, "Cloning, Functional Expression, and Characterization of the Human Prostaglandin E2 Receptor EP2 Subtype".

Receptor & Ion Channel Nomenclature Supplement; Trends in Pharmacological Sciences; Fifth Edition; p. 6, 1994.

Katsuyama et al., FEBS Letters, vol. 344, p. 74, 1994.*

* cited by examiner

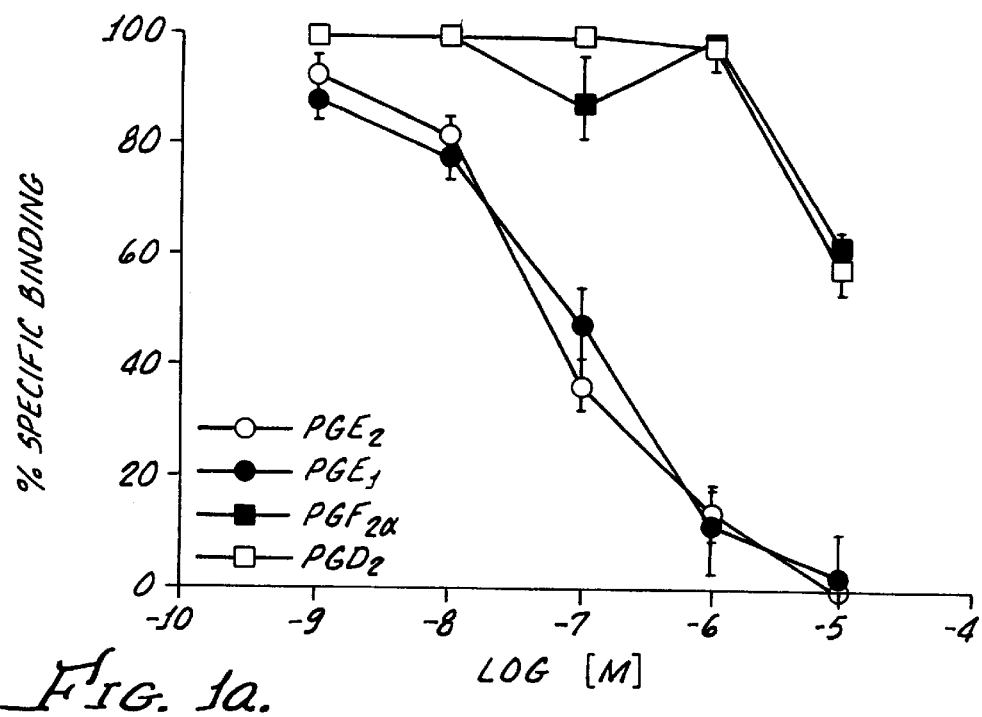
_Fig. 1a._
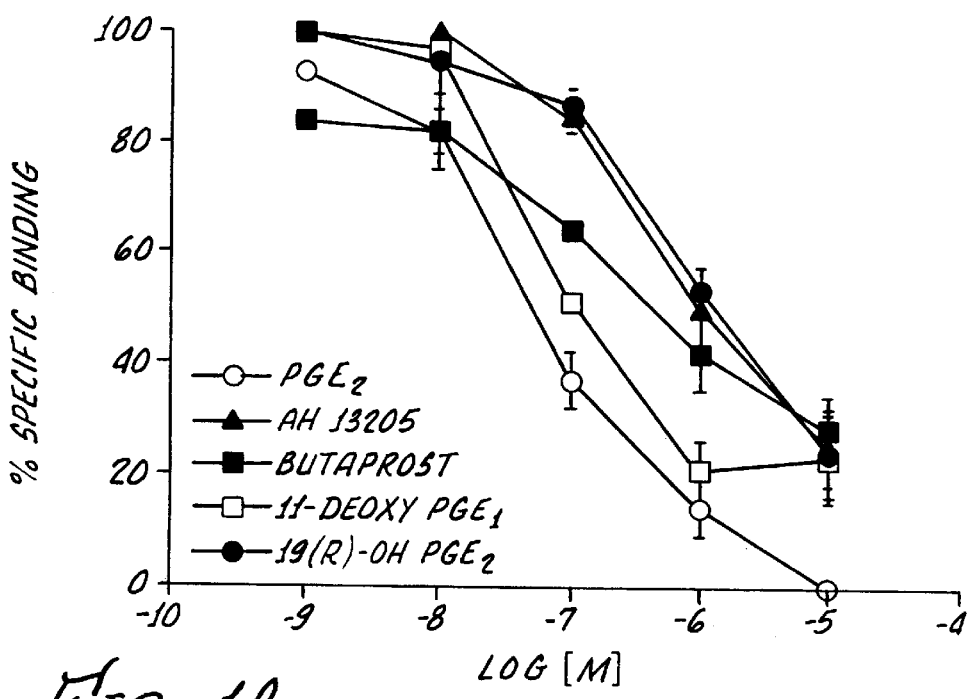
_Fig. 1b._

NUCLEIC ACID ENCODING A HUMAN EP PROSTAGLANDIN RECEPTOR

This application is a continuation-in-part of application Ser. No. 09/019,393 now abandoned, filed Feb. 5, 1998, which was a divisional of application Ser. No. 08/239,431, filed May 5, 1994, now issued as U.S. Pat. No. 5,716,835.

FIELD OF THE INVENTION

This invention relates to the cloning and expression of a novel human prostaglandin receptor. Methods of identifying compounds capable of both binding to and activating this receptor are also disclosed. As determined using the disclosed methods, the receptor exhibits $EP_2$ pharmacology.

BACKGROUND OF THE INVENTION

Prostaglandins are a group of hormone mediators derived from the metabolism of arachidonic acid via the cyclooxygenase enzymatic pathway. In the prostaglandin biosynthetic pathway, arachidonic acid is first converted to prostaglandin endoperoxide H2 ($PGH_2$) by $PGH_2$ synthases followed by the cell-specific isomerization or reduction of $PGH_2$ to the active prostaglandins: $PGD_2$, $PGE_2$, $PGF_{2\alpha}$, prostacyclin ($PGI_2$) and thromboxane ($TxA_2$). Following enzymatic conversion, the major biologically active prostaglandins exert their actions locally on the cells in which they were synthesized (autocrine) and/or on nearby cells (paracrine) through specific G protein-coupled receptors (Smith, (1992) *Am. J. Physiol.,* 263: F181–F191) to either stimulate or inhibit the production of second messengers. Prostaglandins elicit a diverse spectrum of often opposing biological effects including muscle contraction and relaxation, potentiation and inhibition of platelet aggregation, and vasodilation and vasoconstriction. Prostaglandins also exhibit both pro-inflammatory and anti-inflammatory effects. They synergize with other pro-inflammatory mediators such as leukotrienes and bradykinins, but attenuate interleukin-1 (IL-1) production and inhibit various aspects of leukocyte function (Giles, (1990) *Trends Pharmacol. Sci.,* 11:301–304).

Prostaglandin $E_2$ ($PGE_2$) exhibits a broad range of actions in a number of tissues by binding to at least four EP receptor subtypes. It acts through pharmacologically distinct stimulatory ($EP_2$) and inhibitory ($EP_3$) receptor subtypes to stimulate and inhibit cyclic AMP (cAMP) formation, respectively (Sonnenburg, and Smith, (1988) *J. Biol. Chem.,* 263: 6155–6160). $PGE_2$ also stimulates calcium release and protein kinase C activity in the rabbit kidney collecting tubule, most likely by binding to the $EP_1$ receptor subtype which is coupled to stimulation of phospholipase C (Hebert et al., (1990) *Am. J. Physiol.,* 259: F318–F325). The $EP_4$ receptor is an additional subtype of $PGE_2$-sensitive receptor that was recently identified based on agonist effects and blockade by the antagonist AH 23848B (Louttit et al., (1992) *The Eighth International Congress on Prostaglandins and Related Compounds,* Montreal, 258; Coleman et al., (1994) *Prostaglandins,* 47:151–168). Other $PGE_2$-sensitive receptors with distinct agonist pharmacology have been described (Milne et al., (1994) *Br. J. Pharmacol.,* 111:79), but it is not clear whether they are different from the $EP_4$ receptor.

Analogs of $PGE_2$ that are therapeutically useful will elicit or block only a subset of its actions by acting on a single EP receptor subtype. Because prostaglandin receptors are present in tissues in low abundance, the discovery of such analogs is facilitated by the cloning of the receptors. Assigning cloned receptors to a corresponding pharmacologically defined binding site is an iterative process. Defining novel subtypes requires selective compounds, which may only be developed once the receptor is cloned.

Three human receptors that bind $PGE_2$ have been cloned. The $EP_1$ (Funk et al., (1993) *J. Biol. Chem.,* 268: 26767–26772) and $EP_3$ (Regan et al., (1994) *Br. J. Pharmacol.,* 112:377–385) subtypes have been well characterized with subtype-selective compounds, but the pharmacology of the putative $EP_2$ receptor (An et al., (1993) *Biochem. Biophys. Res. Commun.,* 197:263–270; Honda et al., (1993) *J. Biol. Chem.,* 268:7759–7762) is not entirely consistent with the pharmacology derived from tissue models of the $EP_2$ receptor. In particular, the $EP_2$-selective agonist butaprost, is inactive (Gardiner (1986) *Br. J. Pharmacol.,* 87:45–56; Coleman, (1993) in *Eicosanoids and Other Bioactive Lipids in Cancer, Inflammation and Radiation Injury,* Nigan et al., eds., pp. 135–141). The pharmacology of this putative $EP_2$ clone is more similar to that of the $EP_4$ receptor, but it was named before the $EP_4$ receptor had been described.

The deduced protein sequences of the cloned receptors indicate that all are members of the G protein-linked receptor superfamily, having seven putative membrane-spanning hydrophobic domains. The proteins share significant amino acid sequence similarity with other members of this family including the thromboxane (TP) receptor (Hirata et al., (1991) *Nature* 349: 617–620), rhodopsin and the adrenergic receptors.

The cloning of $EP_2$ and/or additional EP receptors will facilitate identification of prostaglandins which can modulate specific effects elicited by this receptor. Since these effects will differ from those activated by other EP receptors, such compounds will have therapeutic utility.

SUMMARY OF THE INVENTION

One embodiment of the present invention is an isolated DNA molecule encoding a novel mammalian prostaglandin EP receptor, herein called HP4 (Human Placental clone Number 4). Preferably, the DNA molecule is human; most preferably, the DNA molecule has the nucleotide sequence shown in SEQ ID NO: 3. According to another aspect of the invention, there is provided an isolated DNA molecule having at least 18 consecutive nucleotides of the DNA molecule encoding the HP4 receptor. In accordance with another aspect of the invention, there is provided an isolated amino acid sequence derived from the HP4 receptor DNA sequence. Preferably, the amino acid sequence is human; most preferably it is SEQ ID NO:4. Advantageously, there is also provided a recombinant construct comprising the HP4 receptor DNA sequence operably linked to a heterologous promoter. In another aspect of this preferred embodiment, there is provided an isolated antibody having binding affinity for the isolated HP4 receptor amino acid sequence. Preferably, the antibody is monoclonal.

Another embodiment of the invention is a method of screening compounds for binding to the prostaglandin HP4 receptor comprising:

transfecting cells with a DNA molecule encoding an HP4 receptor, wherein the DNA molecule is operably linked to a promoter in an expression vector;

culturing the cells to express the HP4 receptor;

incubating at least the cell membranes of the cells in the presence of a labeled compound to be tested for binding affinity to the HP4 receptor; and measuring the amount of label bound to the cell membranes, wherein an increased amount of the label associated with the cell membranes indicates that the compound binds to the receptor.

Preferably, the cells are mammalian; most preferably, they are COS-7 cells. In another aspect of this preferred embodiment, the HP4 receptor is human. Preferably, it is encoded by the polynucleotide of SEQ ID NO:3. Advantageously, the expression vector is mammalian; most preferably, it is pBC12BI. In accordance with this aspect of the invention, the label is radioactive, calorimetric or fluorimetric.

In accordance with another aspect of the invention, there is provided a method of determining the ability of a compound to inhibit ligand binding to the prostaglandin HP4 receptor, comprising:

transfecting cells with a DNA molecule encoding a prostaglandin HP4 receptor, wherein the DNA molecule is operably linked to a promoter in an expression vector;

culturing the cells to express the HP4 receptor;

incubating at least the cell membranes of the cultured cells in the presence of a labeled ligand having binding affinity for the receptor and a test compound; and determining the level of binding of the ligand to the prostaglandin HP4 receptor in the presence of the compound, wherein a lower level of ligand binding in the presence of the compound indicates that the compound binds to the receptor.

Preferably, the cells are mammalian; most preferably, they are COS-7 cells and the HP4 receptor is human. In another aspect of the invention, the HP4 receptor is encoded by the polynucleotide of SEQ ID NO:3. Advantageously, the compound label is radioactive, calorimetric or fluorimetric, the expression vector is mammalian, most preferably pBC12BI, and the ligand is $PGE_2$.

Still another embodiment of the invention is a method for identifying compounds that are agonists of the HP4 prostaglandin receptor, comprising:

transfecting cells with a DNA molecule encoding the HP4 receptor, wherein the DNA molecule is operably linked to a promoter in an expression vector;

preincubating the cells in the presence of a phosphodiesterase inhibitor;

incubating the cells in the presence or absence of a compound to be tested;

lysing the cells; and determining the amount of cyclic AMP produced, wherein an increased amount of cyclic AMP indicates that the compound is an agonist of the receptor.

Preferably, the cells are mammalian; most preferably, they are COS-7 cells. In another aspect of this preferred embodiment, the HP4 receptor is human. In another particularly preferred embodiment, the HP4 receptor is encoded by the polynucleotide of SEQ ID NO:3 . Advantageously, the expression vector is mammalian, most preferably pBC12BI and the phosphodiesterase inhibitor is isobutylmethylxanthine.

According to another aspect of this embodiment, there is provided a cell line in continuous culture expressing the HP4 prostaglandin receptor. Preferably, this HP4 prostaglandin receptor is human; most preferably it is encoded by SEQ ID NO:3. Advantageously, the cells are CHO cells.

BRIEF DESCRIPTION OF THE FIGURES

FIGS. 1A, 1B and 1C illustrate competition curves of $^3H$-$PGE_2$ binding to COS-7 membranes from COS-7 cells transfected with the HP4 receptor cDNA. FIG. 1A compares the displacement of $^3H$-$PGE_2$ by the naturally-occurring prostaglandins $PGE_2$, $PGE_1$, $PGD_2$ and $PGF_2\alpha$. FIG. 1B depicts competition of $^3H$-$PGE_2$ binding by synthetic prostaglandins exhibiting selectivity for the $EP_2$ receptor: A13205, Butaprost, 19(R)-hydroxy $PGE_2$ and 11-deoxy $PGE_1$. FIG. 1C compares the inhibition of radioligand binding by additional PGE analogs 16,16-dimethyl $PGE_2$, MB 28767, sulprostone and $PGE_1$ -1-OH. The y-axis indicates the percentage $^3H$-$PGE_2$ specifically bound and the x-axis indicates the concentration of competitor added (log M). Points represent the mean values +/- standard error from three separate experiments, performed in duplicate.

DETAILED DESCRIPTION OF THE INVENTION

Figure 1C:
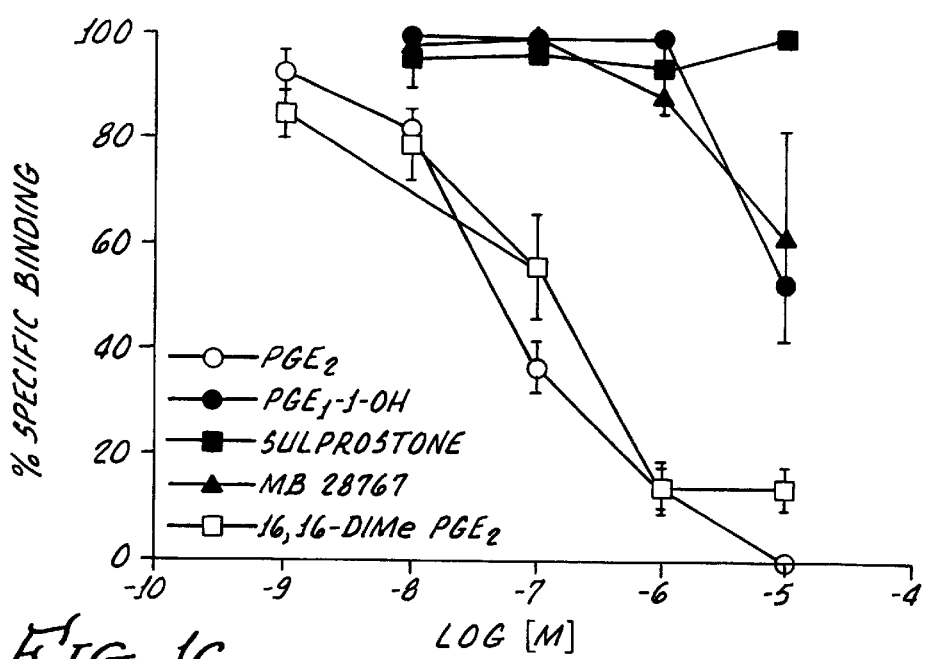

This invention discloses the cloning, sequencing and characterization of a novel human EP prostaglandin receptor, referred to herein as HP4 (Human Placental clone number 4). To characterize the pharmacology of the prostaglandin receptor of the present invention, the gene was transfected into COS-7 cells which lack prostaglandin receptors and competition binding assays using tritiated $PGE_2$ were performed on the plasma membrane fraction (Sugimoto et al., (1992) *J. Biol. Chem.*, 267: 6463–6466). The results suggest that HP4 is a pharmacologically characterized $EP_2$ receptor.

The HP4 gene sequence, fragments thereof, vectors containing this sequence or unique fragments thereof, cells transfected with this sequence or fragments thereof and protein purified from these cells will be useful for studying the pharmacology and the cellular distribution and expression of the HP4 receptor. Since prostaglandins are known to be involved in a variety of biochemical processes including muscle relaxation, platelet aggregation, vasodilation, and inflammation, the receptor of the present invention will be useful for determining the specific processes mediated by the receptor. Since Northern blot analysis demonstrated that HP4 was expressed at high levels in the lung (Example 5), the receptor of the present invention may be important in the development of treatments for bronchopulmonary inflammation and asthma. Polymerase chain reaction (PCR) amplification of the HP4 sequence indicated that it was present in leukocytes (Example 6), suggesting that it may play an important role in regulating inflammation.

The present invention will also facilitate the identification of compounds which specifically bind to this newly-identified prostaglandin receptor. Since this receptor will mediate responses different from those mediated by the other EP receptor subtypes, these compounds will have utility as therapeutic agents. For example, the $EP_2$ -selective agonist AH13205 has been shown to induce bronchodilation and inhibit the release of the inflammatory mediator leukotriene B4 from human neutrophils (Nials et al., (1993) *Cardiovascular Drug Rev.*, 11:165–179). The compound also inhibits the spontaneous contraction of human myometrium (Yeardley et al., (1992) *Br. J. Pharmacol. Proc. Suppl.* 107:90P).

Fragments of the HP4 receptor gene consisting of at least 18 consecutive nucleotides unique to HP4 will be useful as probes and PCR primers for isolating other human prostaglandin receptors, for isolating the corresponding receptor gene from other species and for determining HP4 RNA expression in various human tissues. These oligonucleotides will be useful for in situ hybridization and to probe Northern blots of RNA isolated from various tissues by well-known methods to determine the HP4 receptor cellular distribution.

As specific subsets of the prostaglandin receptor family may be involved in different cellular actions, it is important to identify the receptor subtypes expressed by each cell. It can be appreciated that those of ordinary skill in the art could determine unique fragments of the human HP4 receptor and use these fragments as probes to determine cells expressing the desired prostaglandin receptor gene.

In addition, DNA sequences of 18 nucleotides correspond to six amino acids. Those of ordinary skill in the art will appreciate that a six amino acid peptide, when coupled to an immunogenic carrier protein such as keyhole limpet hemocyanin, can be utilized as an antigen to raise antibodies against HP4 receptor epitopes. Alternatively, the HP4 cDNA or fragments thereof can be expressed and the resulting polypeptide recovered and used as an immunogen. Antibodies against the HP4 receptor protein will allow immunohisto-chemical localization of the protein in cells, tissues and body fluids, thereby providing a means for identification of cells expressing the HP4 receptor subtype.

The use of a number of eukaryotic expression vectors is within the scope of the present invention. Those of ordinary skill in the art will appreciate that once the HP4 receptor clone has been identified and sequenced, it can rapidly be incorporated into almost any desired vector. In the present invention, preferable expression vectors are mammalian, with the most preferable vector being pBC12BI. In addition, the use of yeast, baculovirus and prokaryotic expression vectors is also within the scope of the present invention as is the production of HP4 receptors or fragments thereof in these cell types.

Binding assays using the expressed protein, either in whole transfected cells or in membrane preparations, will be particularly useful for identifying HP4 receptor agonists and antagonists. Although the preferred method of identifying receptor ligands is through radiolabeling, other methods known in the art are also within the scope of the present invention. For instance, well known methods exist for colorimetrically and fluorimetrically labeling compounds. One can also measure functional responses in cells expressing the HP4 receptor protein by using signaling systems including, but not limited to, adenylate cyclase, phosphoinositide hydrolysis, guanylate cyclase, ion fluxes and pH changes. These types of response systems can either be present in the host cell or introduced into the host cell along with the receptor. Although the transfected cells of the present invention are mammalian, any cell type able to express a transfected HP4 gene is contemplated. Transient transfection of HP4 into cells is described below; however, production of stable transfectants expressing the HP4 gene using well-known methods is also contemplated (Example 9).

With the gene sequence determined, mutations can now be introduced to study structure-function relationships as they relate to ligand binding and effector system coupling. For example, point mutations can be introduced into the receptor at various locations by well-known methods. The mutant receptor can then be introduced into cells and the effect of the mutation on ligand binding and signaling pathways can be determined. This analysis will indicate which amino acid residue(s) are involved in ligand binding and effector system coupling, helping to differentiate the functions of EP receptor subtypes, and facilitating the discovery of drugs specific for the HP4 receptor. As a first step in isolating the HP4 receptor gene, a human placental cDNA library was screened under low stringency hybridization conditions with the full-length coding sequence of the human $EP_3$ receptor gene as described in the following example. This gene is described in U.S. patent application Ser. No. 08/155,005, filed Nov. 19, 1993, which is hereby incorporated by reference.

EXAMPLE 1

Cloning of the Human HP4 Receptor by Low Stringency Hybridization

DNA encoding the complete coding sequence of the human $EP_3$ receptor was labeled with $^{32}$P-dATP using a nick-translation kit (Gibco-BRL, Gaithersburg, Md.) and used to screen a λgt11 human placenta cDNA library (Clontech, Palo Alto, Calif.) by plaque hybridization analysis. The library was plated using $E.$ $coli$ Y1090R$^-$cells at a density of approximately 25,000 plaques per plate. A total of 16 plates (400,000 plaques) were used from which impressions were taken using nylon membranes (Colony Plaque Screen, DuPont/NEN). DNA was denatured in 0.5M NaOH, 1.5M NaCl, neutralized in 0.5M Tris-HCl, pH 8.0, 1.5M NaCl and baked at 80° C. for 2 hours. Filters were prehybridized for 2 hours at 37° C. in 50% deionized formamide, 1% sodium dodecyl sulfate (SDS), 1M NaCl, 100 µg/ml sonicated, boiled herring sperm DNA. The $^{32}$P-labeled probe (1×10$^6$ cpm) was added and the filters were hybridized at 37° C. overnight. The filters were then washed for 1 hour at 45° C. in 1× standard saline citrate (SSC), 0.1% SDS, air-dried and exposed to Kodak XAR film (Eastman-Kodak, Rochester, N.Y.) overnight at −70° C.

Polymerase chain reaction (PCR) using primers complementary to λgt11 sequences flanking the cDNA insert region (5'-GACTCCTGGAGCCG-3'; SEQ ID NO:1 and 5'-CGCGGCCAGCGATGG-3'; SEQ ID NO:2) and restriction analysis were used to amplify seven related clones which were placed into three groups based on their size. One member of each group was subcloned into the EcoRI site of pBluescript (Stratagene, La Jolla, Calif.) and its nucleotide sequence determined using the dideoxy chain termination method (United States Biochemical, Cleveland, Ohio). The clones contained overlapping nucleotide sequences. One clone, designated HP4, contained a 2296 nucleotide insert (SEQ ID NO:3) having 156 nucleotides of 5'-untranslated sequence, an open reading frame of 1074 nucleotides encoding a protein of 358 amino acids and 1066 nucleotides of 3'-untranslated sequence. The below-referenced KS/HP4 plasmid has been deposited with the American Type Culture Collection and assigned Accession No. 97472.

The HP4 deduced amino acid sequence was found to have seven hydrophobic putative membrane-spanning domains characteristic of G protein-coupled receptors. The HP4 sequence was aligned with the various putative intracellular loops, extracellular loops, transmembrane domains, and carboxy terminal regions of the thromboxane (TP), $EP_1$, $EP_2$ and $EP_3$ receptors. The alignment revealed a number of conserved residues present in the aligned sequences. In particular, characteristic prostaglandin receptor sequences in the second extracellular loop and seventh transmembrane domain indicated that the isolated HP4 receptor was a prostaglandin receptor. The overall sequence identity of the putative transmembrane regions of HP4 with those of other prostaglandin receptors is 34% for human EP3A, 38% for murine EP2, 37% for murine EP1 and 31% for human TP. Thus, although HP4 possesses conserved sequence motifs found in these previously identified receptors, it is clearly distinct.

A vector for the expression of HP4 in eukaryotic cells was made as follows. PCR was used to amplify nucleotides 124–387 of KS/HP4 (the pBluescript HP4 clone). The primers used were 5'-GATGAGCTCTTTAAAAGGAGGGCGCATCTCTT TTCCAGG-3' (sense; SEQ ID NO:5) and 5'-GGTGAACACCAGCTCGGT-3' (antisense; SEQ ID NO:6). The PCR product was digested with SacI and ligated to the large fragment remaining from the digestion of KS/HP4 with SacI. E. coli cells were transformed and a plasmid with a complete open reading frame in the sense orientation was isolated. The latter was digested with DraI and ligated to the pBC12BI expression vector which had been cleaved with BamHI and HindIII and filled in with the large fragment of DNA polymerase I. E. coli cells were transformed and a plasmid (pBC/HP4) was isolated in which the DraI site adjacent to nucleotide 124 in HP4 was ligated to the HindIII site (nucleotide 314 in pBC12BI). This orientation placed the coding sequences of HP4 (nucleotides 157–1230) downstream (3') of the rous sarcoma virus promoter in pBC12BI. The final construct, therefore, contained 33 bases of HP4 5'-untranslated sequence, the coding region, and 15 bases of 3'-untranslated sequence.

So as to perform the necessary binding assays for demonstrating the ligand specificity of the protein derived from the isolated clone, the HP4 receptor was expressed in transfected COS-7 cells as described in the following example.

EXAMPLE 2

Expression of the Human HP4 Receptor in COS-7 Cell

Monolayers of COS-7 cells (ATCC CRL 1651; 70–80% confluent) were rinsed with Phosphate Buffered Saline (PBS, Ca/Mg-free) in 150×25 mm culture dishes. Ten ml transfection mix, consisting of 5 µg/ml plasmid DNA and 0.5 mg/ml DEAE-dextran in PBS, was added to each dish and cells were incubated for 30 min at 37° C. Nine ml of the solution was removed from each dish followed by the addition of 10 ml of 100 mM chloroquine in Dulbecco's Modified Eagle Medium (DMEM)/5% fetal bovine serum (FBS). The cells were incubated for 2.5 hr at 37° C., the solution aspirated and 10 ml of 10% dimethyl sulfoxide (DMSO) in DMEM/5% FBS was added. After a 2.5 minute incubation at 37° C., the solution was aspirated and 30 ml DMEM/5% FBS was added. The cells were incubated at 37° C. with media changes at 24 and 48 hours. After 72 hours, the media was aspirated and the cells were scraped into cold TME buffer (50 mM Tris-HCl, pH 7.4, 10 mM $MgCl_2$, 1 mM EDTA). The dishes were rinsed with cold TME buffer and the cells combined and placed on ice. To demonstrate the binding of EP receptor ligands to isolated membranes of COS-7 cells expressing the HP4 receptor, membranes were isolated and the binding of radiolabeled ligands was assessed in the presence of increasing concentrations of unlabeled prostaglandin receptor agonists as described in the following example.

EXAMPLE 3

COS-7 Membrane Preparation and Radioligand Binding Assay

Transfected COS-7 cells were homogenized for 30 seconds at approximately 80% power with a Brinkman PT 10/35 Polytron homogenizer. The resulting homogenate was centrifuged at 19,000 rpm for 20 minutes at 4° C. using a Sorvall SS-34 rotor. The membrane pellet was resuspended in cold TME buffer (1 ml per original dish), frozen in liquid nitrogen and stored at −80° C.

Membrane pellets were then diluted in ice-cold 50 mM Tris-HCl buffer at pH 7.4 using a sonicator set at 50 watts. Membrane suspensions (100 µl) were then added to each assay tube to start the binding reaction. Final concentrations of the competition assay were as follows: [$^3$H]-$PGE_2$, 5 nM; 100 µg protein/tube in a total volume of 200 µl. Increasing concentrations of compounds to be tested for competitively inhibiting binding were incubated for 60 minutes at room temperature. Contents were aspirated onto a presoaked ice-cold Whatman GF/B filter using a Brandel Cell Harvester and washed three times with ice-cold assay buffer. The filters were dried, placed in scintillation fluid and counted.

As shown in FIG. 1A, the strongest competitors of [$^3$H]-$PGE_2$ binding were $PGE_2$ itself and $PGE_1$, indicating that the HP4 receptor is in the EP receptor class. Two highly selective agonists for the $EP_2$ receptor, AH13205 and butaprost (Coleman, 1993; Nials et al., 1993; Gardiner, 1986), displaced [$^3$H]-$PGE_2$ binding (FIG. 1B).

The inhibitory potency of AH13205 relative to $PGE_2$ is very similar to their relative potencies in isolated smooth muscle preparations (Nials et al., 1993; Coleman et al., 1994) 19(R)-hydroxy $PGE_2$ and 11-deoxy $PGE_1$, two additional prostanoids reported to exhibit some degree of selectivity for the $EP_2$ receptor (Woodward et al., (1993) *Prostaglandins*, 46:371–383; Dong et al., (1986) *Br. J. Pharmacol.*, 87:97–107), also exhibited competitive activity (FIG. 1B). FIG. 1C shows that the $EP_3$-selective agonist MB 28767, was only slightly active, as was $PGE_1$ -1-OH. Sulprostone, an agonist at both the $EP_1$ and $EP_3$ receptors (Coleman, (1993)), was inactive. 16,16-dimethyl $PGE_2$, which stimulates the $EP_4$ receptor in the rabbit jugular vein (Milne et al., 1994), was active. These results are consistent with the HP4 receptor being the pharmacologically defined $EP_2$ receptor rather than the cloned receptors that were previously designated $EP_2$ (An et al., 1993; Honda et al., 1993). However, identity of HP4 with the $EP_4$ receptor or an additional EP receptor cannot be ruled out.

The native $EP_2$ receptor is coupled through a G protein to the stimulation of adenylate cyclase, an enzyme which transiently associates with the G protein upon prostaglandin binding and converts ATP to cAMP. To determine whether the cloned HP4 receptor could bind prostaglandins and mediate changes in cAMP levels, the HP4 cDNA was transfected into COS-7 cells as described in Example 2. The effect of PGE2 and prostaglandin analogs on cAMP accumulation is described in the following example.

EXAMPLE 4

$PGE_2$ Treatment and cAMP Assay on HP4-transfected COS Cells

HP4-transfected COS-7 cells, prepared as described in Example 2, were cultured in DMEM containing 10% FCS, 100 units/ml penicillin, 100 µg/ml streptomycin. Cells were plated in 24 well plates (Falcon Labware, approximately 2 $cm^2$/well) 24 hours after transfection. Cells were trypsinized and resuspended in a small volume of medium (2–3 ml), counted using a hemocytometer and diluted to 7–8×10$^4$ cells/ml (DMEM/5% FCS). One ml cell suspension was added to each well. After 24 hours at 37° C., the medium was changed and on the following day, cells were rinsed briefly with 1 ml of serum-free medium and were pre-incubated for 1 minute with 400 μl/well of serum-free medium containing 100 μg/ml isobutylmethylxanthine (IBMX), an inhibitor of phosphodiesterase, an enzyme which degrades cAMP. One hundred μl of the indicated concentrations (FIG. 2) of $PGE_2$ or prostaglandin analogs were added to each well for 3 minutes at 37° C. Drug solutions were aspirated and 150 μl TE solution (50 mM Tris-HCl, pH 7.5, 4 mM EDTA) was added. Cells were scraped into TE, boiled for 5 min. in microcentrifuge tubes and placed on ice. Samples were then centrifuged for 10 min at 14,000 rpm to obtain a clarified cytosolic fraction. The amount of cAMP was quantified as follows. Assay standards of 0, 0.125, 0.25, 0.5, 1, 2, 4, 8, 16, 32 and 64 pmol cAMP were prepared by diluting 2X concentrations 1:1 with TE. Fifty μl assay standard or cytosol was then combined with 50 μl [$^3$H]-cAMP. One hundred μl (6 μg) protein kinase A (PKA), an enzyme which binds cAMP, was then added to each tube. One control tube received no PKA, only 100 μl 0.1 BSA/Tris. Samples were vortexed, placed on ice for two hours and 100 μl 2% BSA-2.6% charcoal suspension was added which will bind the PKA-cAMP complex, but not the free cAMP. Samples were vortexed, centrifuged for 45 seconds, placed on ice and 200 μl supernatant transferred to scintillation vials for counting. Counts in the drug-treated samples were compared to counts in the standard tubes to determine the amounts of cAMP. More [$^3$H]-cAMP remaining in the supernatant indicates that more cAMP was synthesized in response to the drug and competitively inhibits binding of the labeled cAMP to PKA.

Figure 2:
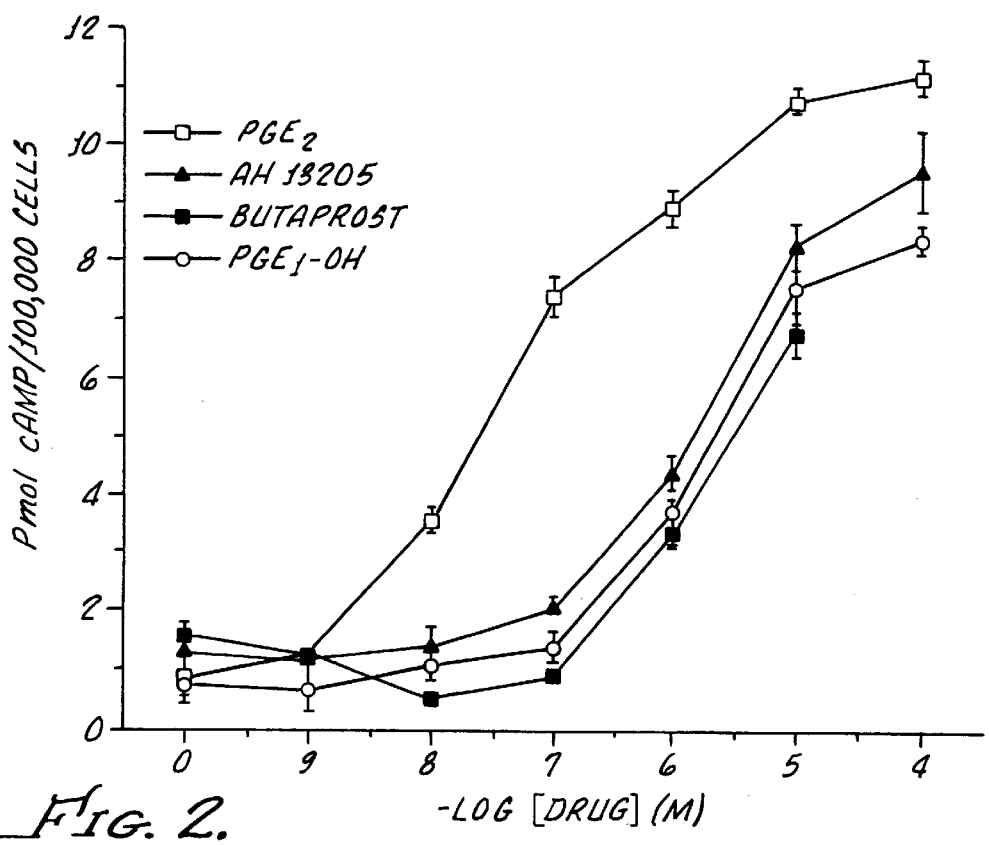
FIG. 2 shows the effects of prostaglandin treatment on cAMP levels in COS-7 cells, after transient transfection with DNA encoding the human HP4 receptor. Subsequent to transfection, cells were stimulated with either $PGE_2$, AH13205, butaprost or $PGE_1$ -1-OH. The drug concentration (-log M) is shown on the x-axis and the amount of cAMP produced (pmol/$10^5$ cells) is shown on the y-axis.

The results indicated that $PGE_2$ treatment resulted in significantly increased cAMP levels in HP4-transfected COS cells (FIG. 2). $PGE_2$ could potently stimulate cAMP formation followed by AH13205, butaprost and $PGE_1$ -1-OH, in decreasing order of potency. These results are similar to the results obtained in the radioligand binding studies and lend further support to the pharmacological similarity of HP4 with the pharmacologically defined $EP_2$ subtype.

The expression of HP4 mRNA in various human tissues was then determined as described below.

EXAMPLE 5

Tissue Distribution of the HP4 Prostaglandin Receptor Gene

A multiple human tissue Northern blot (Clontech, Palo Alto, Calif.) consisting of RNA isolated from heart, brain, placenta, lung, liver, kidney and pancreas was prehybridized in 4.4.times.SSPE, 44% deionized formamide, 8.8× Denhardt's solution, 1.75% SDS and 88 μg/ml denatured herring sperm DNA at 42° C. with constant rotation. The prehybridization solution was removed and the filter was incubated in fresh solution containing 1.5×10$^6$ cpm/ml nick-translated HP4 cDNA prepared with a kit (Gibco BRL, Gaithersburg, Md.) at 42° C. overnight with constant rotation. The blot was washed six times in 2×SSC, 0.5% SDS at room temperature for 5 minutes each with constant agitation. The blot was then washed in 0.1×SSC, 0.1% SDS at 50° C. for 40 minutes with one change of solution, dried and exposed to x-ray film. The lanes containing the placenta and lung RNA were strongly positive. Since this receptor is expressed at high levels in the lung, it may play a role in regulating airway opening and inflammation in respiratory disorders such as asthma and emphysema.

Because the human uterus (Senior et al., (1991) *Br. J. Pharmacol.*, 102:747–753) and human neutrophils (Nials et al., 1993) are $EP_2$-active tissues, as well as the lung, PCR amplification of RNA was then performed to determine whether HP4 was expressed in human uterus, human placenta, human promyelocytic leukemia HL60 cells (ATCC CCL 240) and/or human acute T-cell leukemia Jurkat T-cells (ATCC TIB 152) as described below.

EXAMPLE 6

PCR Amplification of HP4 from Human Cells and Tissues

Sense (5'-CTTACCTGCAGCTGTACG-3'; SEQ ID NO:7) and antisense (5'-GATGGCAAAGACCCAAGG-3'; SEQ ID NO:8) primers corresponding to the second extra-cellular loop and the seventh transmembrane region, respectively, of the human HP4 receptor clone were used in PCR reactions. Control sense (5'-ATCTGGCACCACACCTTCTACAATGAGCTGCG-3'; SEQ ID NO:9) and antisense (5'-CGTCATACTCCTGCTTGCTGATCCACATCTGC; SEQ ID NO:10) primers to β-actin were also used. RNA was isolated from tissues and cell lines by techniques well known in the art.

The PCR reactions contained 1 μl of the RT reaction, 36.5 μl water, 5 μl 10×buffer (Perkin-Elmer, Norwalk, Conn.), 3 μl MgCl2 (25 mM), 2 μl dNTPs (1.25 mM each), 1 μl tetramethyl ammonium chloride (TMA; 2.5 mM), 0.625 μl sense primer (25 μM), 0.625 μl antisense primer (25 μM), 0.25 μl Taq polymerase (Perkin-Elmer, 5 units/μl) in a final volume of 50 μl. The denaturation step was performed at 94° C. for 2 min, followed by 35–40 cycles at 94° C. for 15 sec, 60° C. for 15 sec and 72° C. for 2 min. A 6 min incubation at 72° C. completed the reaction.

Half of the PCR reactions (25 μl) were analyzed by electrophoresis on a 1.5% agarose gel and staining with ethidium bromide. These samples were run in parallel with positive controls using plasmid DNA as a template and negative controls which did not contain a DNA template. A fragment having the predicted molecular weight based on the HP4 sequence (368 base pairs) was observed in RNA isolated from placenta, uterus, HL 60 cells and Jurkat T-cells. No fragments were amplified in the absence of a DNA template. The HP primers do not amplify a product from human genomic DNA, probably because there is an intron in between the two primers. Thus, the PCR products reflect the presence of mRNA encoding HP4 and not of contaminating genomic is DNA.

To estimate the relative level of HP expression from these sources, the same cDNAs were amplified for 25–30 cycles using the actin primers, SEQ ID NOS:9 and 10. Comparison of the product yields with actin and HP primers shows that HP4 is expressed in to human uterus, placenta and HL-60 cells, but only at low levels in Jurkat T-cells. Thus, this receptor may also regulate inflammatory processes in disorders such as emphysema and arthritis.

To further characterize the human HP4 receptor, polyclonal antibodies are generated as described in the following example.

EXAMPLE 7

Production of Polyclonal Antibodies Against the Human HP4 Receptor

PCR primers are used to amplify an approximately 126 nucleotide region corresponding to the hydrophilic amino acid segments connecting the fifth and sixth membrane spanning domains of the human HP4 receptor. The resulting PCR product is purified by agarose gel electrophoresis, cloned into an expression plasmid such as pGEX (Pharmacia, Piscataway, N.J.) and used to transform E. coli by standard procedures. The positive clones are identified and induced to express the fusion protein, which is purified by well known methods.

The purified fusion protein is injected into the breast muscle of chickens (50–100 μg/injection) with booster injections given at two week intervals. The IgY antibodies are purified from the egg yolks by well known methods and their specificity determined by immunoblotting of tissue extracts.

In addition, monoclonal antibodies to the human HP4 receptor to can be prepared as discussed below.

EXAMPLE 8

Production of Monoclonal Antibodies Against the Human HP4 Receptor

The HP4 receptor-transfected COS-7 cell lysate, isolated as described in Example 7, is centrifuged to isolate membranes. The isolated membranes are injected in Freund's complete adjuvant into mice. After 9 booster injections over a three week period, the spleens are removed and resuspended in PBS. The resuspended spleen cells are mixed (approximately 4:1) with SP2/0 myeloma cells. Polyethylene glycol is added to fuse the myeloma and spleen cells, and the hybridomas are selected in HAT medium. The fused cells are aliquoted to allow growth of only one cell in each well of a 96 well microtiter plate. Each cell is expanded, the media removed and secreted proteins are labeled with $^{125}$I. The labeled media from each well is used to probe a Western blot of transfected and untransfected COS-7 cell membranes.

The desired hybridoma produces a monoclonal antibody that strongly binds a protein band in a transfected COS-7 cell membrane lane on a Western blot, but does not bind to any other protein in that lane or in an untransfected COS-7 cell membrane lane (control). This method can be used to detect those cells expressing the human HP4 receptor.

EXAMPLE 9

Production of Stably-transfected Cells

To produce CHO cells stably transfected with the human HP4 gene, CHO cells are cotransfected with 10–30 μg human HP4 and 1–5 μg pSV2Neo carrying the neomycin resistance gene by calcium phosphate precipitation (Graham and Van der Eb, (1973) Virology, 52: 456–467). The cells are then subjected to selection with 600 μg/ml genetecin (G418; Gibco). The resistant colonies are selected, expanded and screened for receptor expression using [$^3$H]-PGE$_2$ binding as described in Example 3.

A murine homolog of the human HP4 prostaglandin receptor gene is isolated as described below.

EXAMPLE 10

Isolation of a Murine HP4 Prostaglandin Receptor Gene

The HP4 gene, isolated as described in Example 1, is digested with restriction enzymes by well-known methods to obtain a DNA segment of approximately 1–1.5 kilobases. This segment is nick-translated using a kit (Gibco BRL, Gaithersburg, Md.) and [$^{32}$P]-dATP, then used to screen mouse cDNA libraries which are available from several commercial sources including Clontech (Palo Alto, Calif.). The positive clones are sequenced and aligned with the HP4 sequence using one of a number of computer sequence alignment programs well-known in the art to determine whether the mouse clone shares significant sequence identity with human HP4

EXAMPLE 11

Antisense Oligonucleotides Directed to Human HP4 Prostaglandin Receptor

Antisense agents directed to human HP4 prostaglandin receptor mRNA may used to attenuate the effects of endogenous HP4 receptor agonists in patients having conditions including, without limitation, chronic asthma or immunosuppression. Such antisense agents include oligonucleotides that comprise "native" deoxyribonucleotides, or that may comprise modified nucleotides. Modified nucleotides are monomeric compounds not usually (or ever) found in nature which have the ability to form hydrogen-bonded base pairs with a nucleotide base and are further able to be heteropolymerized into a linear oligonucleotide or oligonucleotide analog. Examples of modified bases include, for example, 2'methoxyribonucleotides, methylphosphonate nucleotides, and phosphorothioate nucleotides. Additionally, antisense agents may comprise oligonucleotide analogs such as peptide nucleic acids (PNAs); for the purpose of this application, PNAs and similar oligonucleotide analogs shall be considered to consist of modified nucleotides. Numerous additional modified nucleotides exist and are known to the person of skill in the art; such additional modified nucleotides are intended to fall within the scope of this term. As used herein, the term "oligonucleotide" shall include oligonucleotide analogs such as those mentioned above, and shall mean a short linear molecule having the ability to form hydrogen bonds with the nucleotide bases of a specific segment of a single stranded nucleic acid molecule. Depending upon the specific type of modification, modified antisense agents may be more resistant to nuclease digestion, may have a greater melting temperature as ($T_m$), and/or a greater mRNA specificity than oligonucleotides made of unmodified nucleotides. These properties can result in an increased ability to prevent expression of a target protein. The antisense agents described herein function to bind HP4 receptor DNA and/or mRNA and to prevent transcription or translation by any of a number of mechanisms such as the recruitment of RNase H activity to a DNA:RNA hybrid with subsequent destruction of the RNA or through steric hindrance by the antisense agent of ribosome access to the 5' translation initiation region of the target gene.

Antisense oligonucleotides may be delivered to the target cell as the "naked" oligonucleotide by injection, infusion, or inhalation into the target tissue. However (particularly in the case of charged antisense agents) entry of the antisense agents into the cell through the apolar portions of the cell membrane can be problematic, and can result in a decrease in delivery and effectiveness. To overcome this problem, alternative delivery strategies have been devised.

One such strategy involves encasing the antisense agent in a liposome. Liposomes are artificial membrane analogs composed of lipids having polar headgroups. Particularly preferred for negatively charged antisense agents are liposomes containing cationic lipids, which function to neutralize the charge of the antisense agent and are attracted by the negatively charged outer plasma membrane. Additionally, liposomes may contain other types of lipids such as sterols (e.g. vitamin D₃ or cholesterol). The liposomes are formed by sonication of a lipid-containing solution or extrusion of the solution through a microbial filter. The advantage of using liposomes for drug delivery is that the liposome can fuse with the plasma membrane or be taken up by the cell through endocytosis, resulting in the liberation of the antisense agent within the cytoplasm of the cell. Certain pH-sensitive lipids, such as DOPE (dioleoylphosphatidyl-ethanolamine) will destabilize at acidic pH, thus aiding in the liberation of the antisense agent within the cell. The person of ordinary skill in the art will be familiar with liposome technology; additionally a large number of references are available in the scientific literature that deal with strategies for drug delivery using liposomes. See e.g., Felgner et al., U.S. Pat. No. 5,264,618, which is incorporated herein by reference. Such therapeutic agents in liposome formulations may be delivered by means including injection, infusion, inhalation, and topical application.

An alternative strategy for the delivery of antisense agents is the use of vectors, such as vectors derived from a virus, which will deliver a translatable nucleic acid region containing a selected short portion of the target nucleic acid sequence to the cell along with a strong promoter, and permit the transcription of this nucleic acid region to form multiple complementary single-stranded antisense RNA copies thereof. These RNA molecules would then act to hybridize with HP4 mRNA, thus preventing translation of the mRNA.

Depending upon the nature of the vector and its size, it could also be engineered to contain a foreign, specific RNA polymerase gene, such as, without limitation, the T4 bacteriophage RNA polymerase gene. Since T4 RNA polymerase is quite fastidious in its specificity for its own promoter, in such a system the transcriptional effects of the vector could be effectively limited to the desired therapeutic effect by placing the translatable nucleic acid region under control of a 5' T4 promoter sequence. The inclusion of the T4 RNA polymerase gene within the vector, and expression of T4 RNA polymerase within the host cell, would ensure that a large number of copies of the antisense agents would be produced from each vector molecule. Other RNA polymerase genes having strong specificity for particular promoter sequences may also be used, and are known to those of skill in the art.

Viral vectors may be derived from viruses such as, without limitation, adenovirus, adeno-associated virus (AAV-2), and various retroviruses. Of course, other applicable viral vectors are available or can be envisioned by the person of ordinary skill in the art; the vectors mentioned herein are by way of illustration rather than limitation.

Each prospective vector has its own benefits and deficits. For example, adenovirus infections are common and relatively benign in humans; this virus is one of those responsible for the common cold. The virus contains a double-stranded DNA genome. After deletion of non-essential genes, the virus is able to carry about 8 kilobase pairs of an exogenous double-stranded DNA insert. This amount would be more than adequate to carry the antisense agent or its complementary template as well as necessary regulatory sequences, such as a strong promoter. However, the immunogenicity of adenovirus is relatively high. Additionally, adenovirus does not stably integrate into the host chromosome, and therefore its therapeutic effect is relatively transient; of course, this result may be advantageous when it is desired that the therapeutic effect of the antisense agent be temporary. Certain constructs of adenovirus (and other gene transfer vectors) have been made "replication deficient" in order to control the extent and duration of infection, and to minimize the spread of the recombinant virus.

AAV-2 also commonly infects humans but is not known to cause a disease. The virus is quite small, and therefore it is relatively non-immunogenic. However, the small size also means that there is less room for packaging a therapeutic nucleic acid sequence region and any necessary regulatory sequences or genes such as an RNA polymerase gene. Wild-type AAV-2 stably integrates at a specific site in human chromosome 19, however the gene responsible for this stable integration is deleted in recombinant versions of the viral genome, and this property is therefore lost. Over a period of time recombinant AAV-2 appears to randomly integrate into the host chromosome. Also, optimal gene expression is only seen after 3–5 weeks when using such vectors.

Retroviruses such as modified Moloney murine leukemia virus have also been used as the raw materials of engineered transfer vectors. The virus gives rise to a minimal immunological response. Retroviral vectors specifically infect dividing cells, and for this reason they appear as attractive candidates as vectors against cancers. Moreover, retroviral vectors stably integrate into the chromosomes of the host cell, providing the potential for long term expression of the passenger nucleic acid, and thus reducing the need for frequent re-introduction of the vector. Construction of retroviral vectors has involved removal of the gag, pol, and env genes from the DNA provirus to make-room for the gene(s) of therapeutic interest, up to about 8 kilobases of inserted nucleic acid. This process makes the vector replication-deficient, and the virus particles are propagated in special "packaging" cell lines that contain the genes missing from the vector. See e.g., *The Pharmacological Basis of Therapeutics* Ch. 5 (Hardman et al. ed., 9$^{th}$ ed. 1996), the disclosure of which is hereby incorporated by reference as part of this disclosure.

Thus, in one aspect of the present invention, a patient having severe chronic asthma is treated with a liposome composition containing an HP4 prostaglandin receptor-directed antisense agent in an inhalant as follows. A preparation of a synthetic oligonucleotide analog containing 2' O methylribofuranosyl ("2'methoxy") residues is prepared. The antisense agent is constructed to be able to hybridize with the 10 nucleotides immediately 5' to the first ATG codon of the coding sequence for the HP4 receptor, and with the first 12 nucleotides of the coding region of the HP4 gene. General methods for synthesizing oligonucleotides are well known, and methods for synthesizing oligonucleotide analogs containing 2,methoxyribonucleotides are disclosed in, e.g., Becker et al., WO 98/02582, which is hereby incorporated by reference herein in its entirety.

A liposome preparation is made as follows: a total of 80 micromoles (total lipids) of a mixture of lipids including DOPE (dioleoylphosphatidyl-ethanolamine), oleic acid and Vitamin D₃ is made in an organic solvent in a molar ratio of 10:5:2, then the preparation is lyophilized. The lyophilizate is mixed with an aqueous solution of the purified oligonucleotide. Liposomes are formed by extrusion of the mixture through a 5 micron filter.

The liposome solution is then delivered once daily for one week using an atomizing inhaler. The combination of inhaler delivery volume and concentration of the liposomal solution is designed to deliver an effective dose of the therapeutic antisense agent to lung tissue, thus resulting in the modulation of eosinophil recruitment to lung tissue and of contraction of the smooth muscle of the airways. Upon examination of the patient one week following the initiation of treatment, airway inflammation and bronchiospasm is decreased as compared to a patient receiving only a placebo control.

Other applications and modes of delivery of antisense agents will be apparent to those of skill in the art.

While particular embodiments of the invention have been described in detail, it will be apparent to those skilled in the art that these embodiments are exemplary, rather than limiting, and the true scope of the invention is that defined in the following claims.

What is claimed is:

1. An isolated polypeptide comprising a full length human prostaglandin HP4 receptor, wherein the amino acid sequence of said receptor is encoded by a nucleotide sequence contained within an open reading frame of plasmid HS/HP4, ATCC® accession number 97472.

2. A polypeptide comprising a fragment of the human prostaglandin HP4 receptor of claim 1, wherein said fragment comprises an amino acid sequence encoded by at least 18 consecutive nucleotides of a nucleotide sequence region flanked by primers of sequence SEQ ID NO: 5 and SEQ ID NO: 6 and wherein said polypeptide binds an antibody which binds the full-length human prostaglandin HP4 receptor of claim 1.

3. The polypeptide of claim 2 comprising at least one immunogenic carrier protein joined thereto.

4. The polypeptide of claim 3 wherein said at least one immunogenic carrier protein comprises keyhole limpet hemacyanin.

5. The polypeptide of claim 2 further comprising a fusion protein.

6. The polypeptide of claim 3 further comprising a fusion protein.

7. A composition comprising an isolated fragment of the human prostaglandin HP4,receptor which comprises an amino acid sequence region of at least six consecutive amino acids of a polypeptide encoded by a nucleotide sequence contained within an open reading frame of plasmid KS/HP4, ATCC® accession number 97472, which nucleotide sequence is flanked by PCR primers of sequence SEQ ID NO: 5 and SEQ ID NO: 6, and wherein said polypeptide binds an antibody which binds the full length human prostaglandin HP4 receptor encoded by said plasmid.

8. The composition of claim 7 comprising an immunogenic carrier protein, wherein said carrier protein is joined to the isolated peptide of claim 7.

9. The composition of claim 8 wherein said immunogenic carrier protein is keyhole limpet hemocyanin.

10. The polypeptide of claim 2, in which said nucleotide sequence region is a nucleic acid amplified by PCR primers of sequence SEQ ID NO: 5 and SEQ ID NO: 6.

11. The composition of claim 7, wherein said nucleotide sequence is contained in a nucleic acid amplified by PCR primers of sequence SEQ ID NO: 5 and SEQ ID NO: 6.

12. The composition of claim 7, wherein said amino acid sequence region is further encoded by a nucleotide sequence contained in a nucleic acid amplified by PCR primers of SEQ ID NO:7 and SEQ ID NO:8.

13. The composition of claim 11 comprising an immunogenic carrier protein, wherein said carrier protein is joined to the isolated peptide of claim 11.

14. The composition of claim 13 wherein said at least one immunogenic carrier protein comprises keyhole limpet hemacyanin.

15. The composition of claim 12 comprising an immunogenic,carrier protein, wherein said carrier protein is joined to the isolated peptide of claim 12.

16. The composition of claim 10 comprising at least one immunogenic carrier protein joined thereto.

17. The composition of claim 16 wherein said at least one immunogenic carrier protein comprises keyhole limpet hemacyanin.

* * * * *

UNITED STATES PATENT AND TRADEMARK OFFICE
CERTIFICATE OF CORRECTION

PATENT NO. : 6,395,878 B1
DATED : May 28, 2002
INVENTOR(S) : Regan et al.

It is certified that error appears in the above-identified patent and that said Letters Patent is hereby corrected as shown below:

Column 3,
Line 9, delete "calorimetric" and insert in place thereof -- colorimetric --
Line 32, delete "calorimetric" and insert in place thereof -- colorimetric --

Column 6,
Line 18, delete "$^{32}$P-dATP" and insert in place thereof -- $^{32}$p-dATP --

Column 14,
Line 53, delete "2," and insert in place thereof -- 2' --

Column 23,
Line 20, delete "further".
Line 25, delete "HP4, receptor" and insert in place thereof -- HP4 receptor --

Signed and Sealed this

Twenty-third Day of July, 2002

Attest:

Attesting Officer

JAMES E. ROGAN
*Director of the United States Patent and Trademark Office*

SEQUENCE LISTING

```
<160> NUMBER OF SEQ ID NOS: 10

<210> SEQ ID NO 1
<211> LENGTH: 14
<212> TYPE: DNA
<213> ORGANISM: Homo sapiens

<400> SEQUENCE: 1
gactcctgga gccg                                                         14

<210> SEQ ID NO 2
<211> LENGTH: 15
<212> TYPE: DNA
<213> ORGANISM: Homo sapiens

<400> SEQUENCE: 2
cgcggccagc gatgg                                                        15

<210> SEQ ID NO 3
<211> LENGTH: 2296
<212> TYPE: DNA
<213> ORGANISM: Homo sapiens
<220> FEATURE:
<221> NAME/KEY: CDS
<222> LOCATION: (157)...(1233)

<400> SEQUENCE: 3
gggccgccgt cggcgcgctg ggtgcgggaa gggggctctg gatttcggtc c ctggggttt      60 ttcctctgag tctcggaacg ctccagctct cagaccctct tcctcccagg t aaaggccgg    120 gagaggaggg cgcatctctt ttccaggcac cccacc atg ggc aat gcc tcc aat       174
                                        Met Gly Asn Ala Ser Asn
                                          1               5 gac tcc cag tct gag gac tgc gag acg cga c ag tgg ctt ccc cca ggc      222
Asp Ser Gln Ser Glu Asp Cys Glu Thr Arg G ln Trp Leu Pro Pro Gly
            10                  15                  20 gaa agc cca gcc atc agc tcc gtc atg ttc t cg gcc ggg gtg ctg ggg      270
Glu Ser Pro Ala Ile Ser Ser Val Met Phe S er Ala Gly Val Leu Gly
        25                  30                  35 aac ctc ata gca ctg gcg ctg ctg gcg cgc c gc tgg cgg ggg gac gtg      318
Asn Leu Ile Ala Leu Ala Leu Leu Ala Arg A rg Trp Arg Gly Asp Val
    40                  45                  50 ggg tgc agc gcc ggc cgc agg agc tcc ctc t cc ttg ttc cac gtg ctg      366
Gly Cys Ser Ala Gly Arg Arg Ser Ser Leu S er Leu Phe His Val Leu
55                  60                  65                  70 gtg acc gag ctg gtg ttc acc gac ctg ctc g gg acc tgc ctc atc agc      414
Val Thr Glu Leu Val Phe Thr Asp Leu Leu G ly Thr Cys Leu Ile Ser
                75                  80                  85 cca gtg gta ctg gct tcg tac gcg cgg aac c ag acc ctg gtg gca ctg      462
Pro Val Val Leu Ala Ser Tyr Ala Arg Asn G ln Thr Leu Val Ala Leu
            90                  95                 100
```

-continued

| | |
|---|---|
| gcg ccc gag agc cgc gcg tgc acc tac ttc g ct ttc gcc atg acc ttc<br>Ala Pro Glu Ser Arg Ala Cys Thr Tyr Phe A la Phe Ala Met Thr Phe<br>105 110 115 | 510 |
| ttc agc ctg gcc acg atg ctc atg ctc ttc g cc atg gcc ctg gag cgc<br>Phe Ser Leu Ala Thr Met Leu Met Leu Phe A la Met Ala Leu Glu Arg<br>120 125 130 | 558 |
| tac ctc tcg atc ggg cac ccc tac ttc tac c ag cgc cgc gtc tcg cgc<br>Tyr Leu Ser Ile Gly His Pro Tyr Phe Tyr G ln Arg Arg Val Ser Arg<br>135 140 145 150 | 606 |
| tcc ggg ggc ctg gcc gtg ctg cct gtc atc t at gca gtc tcc ctg ctc<br>Ser Gly Gly Leu Ala Val Leu Pro Val Ile T yr Ala Val Ser Leu Leu<br>155 160 165 | 654 |
| ttc tgc tcg ctg ccg ctg ctg gac tat ggg c ag tac gtc cag tac tgc<br>Phe Cys Ser Leu Pro Leu Leu Asp Tyr Gly G ln Tyr Val Gln Tyr Cys<br>170 175 180 | 702 |
| ccc ggg acc tgg tgc ttc atc cgg cac ggg c gg acc gct tac ctg cag<br>Pro Gly Thr Trp Cys Phe Ile Arg His Gly A rg Thr Ala Tyr Leu Gln<br>185 190 195 | 750 |
| ctg tac gcc acc ctg ctg ctg ctt ctc att g tc tcg gtg ctc gcc tgc<br>Leu Tyr Ala Thr Leu Leu Leu Leu Ile V al Ser Val Leu Ala Cys<br>200 205 210 | 798 |
| aac ttc agt gtc att ctc aac ctc atc cgc a tg cac cgc cga agc cgg<br>Asn Phe Ser Val Ile Leu Asn Leu Ile Arg M et His Arg Arg Ser Arg<br>215 220 225 230 | 846 |
| aga agc cgc tgc gga cct tcc ctg ggc agt g gc cgg ggc ggc ccc ggg<br>Arg Ser Arg Cys Gly Pro Ser Leu Gly Ser G ly Arg Gly Gly Pro Gly<br>235 240 245 | 894 |
| gcc cgc agg aga ggg gaa agg gtg tcc atg g cg gag gag acg gac cac<br>Ala Arg Arg Arg Gly Glu Arg Val Ser Met A la Glu Glu Thr Asp His<br>250 255 260 | 942 |
| ctc att ctc ctg gct atc atg acc atc acc t tc gcc gtc tgc tcc ttg<br>Leu Ile Leu Leu Ala Ile Met Thr Ile Thr P he Ala Val Cys Ser Leu<br>265 270 275 | 990 |
| cct ttc acg att ttt gca tat atg aat gaa a cc tct tcc cga aag gaa<br>Pro Phe Thr Ile Phe Ala Tyr Met Asn Glu T hr Ser Ser Arg Lys Glu<br>280 285 290 | 1038 |
| aaa tgg gac ctc caa gct ctt agg ttt tta t ca att aat tca ata att<br>Lys Trp Asp Leu Gln Ala Leu Arg Phe Leu S er Ile Asn Ser Ile Ile<br>295 300 305 310 | 1086 |
| gac cct tgg gtc ttt gcc atc ctt agg cct c ct gtt ctg aga cta atg<br>Asp Pro Trp Val Phe Ala Ile Leu Arg Pro P ro Val Leu Arg Leu Met<br>315 320 325 | 1134 |
| cgt tca gtc ctc tgt tgt cgg att tca tta a ga aca caa gat gca aca<br>Arg Ser Val Leu Cys Cys Arg Ile Ser Leu A rg Thr Gln Asp Ala Thr<br>330 335 340 | 1182 |
| caa act tcc tgt tct aca cag tca gat gcc a gt aaa cag gct gac ctt<br>Gln Thr Ser Cys Ser Thr Gln Ser Asp Ala S er Lys Gln Ala Asp Leu<br>345 350 355 | 1230 |
| tga ggtcagtagt ttaaaagttc ttagttatat agcatctgga agatcatt tt | 1283 |
| gaaattgttc cctggagaaa tgaaaacagt gtgtaaacaa aatgaagctg c cctaataaa | 1343 |
| aaggagtata caaacattta agctgtggtc aaggctacag atgtgctgac a aggcacttc | 1403 |
| atgtaaagtg tcagaaggag ctacaaaacc taccctcaat gagcatggta c ttggccttt | 1463 |
| ggaggaacaa tcggctgcat tgaagatcca gctgccatt gatttaagct t tcctgttga | 1523 |
| atgacaaagt atgtggtttt gtaatttgtt tgaaacccca aacagtgact g tactttcta | 1583 |
| ttttaatctt gctactaccg ttatacacat atagtgtaca gccagaccag a ttaaacttc | 1643 |
| atatgtaatc tctaggaagt caatatgtgg aagcaaccaa gcctgctgtc t tgtgatcac | 1703 |

```
ttagcgaacc ctttatttga acaatgaagt tgaaaatcat aggcaccttt t actgtgatg    1763 tttgtgtatg tgggagtact ctcatcacta cagtattact cttacaagag t ggactcagt    1823 gggttaacat cagttttgtt tactcatcct ccaggaactg caggtcaagt t gtcaggtta    1883 tttattttat aatgtccata tgctaatagt gatcaagaag actttaggaa t ggttctctc    1943 aacaagaaat aatagaaatg tgtcaaggca gttaattctc attaatactc t tattatcct    2003 atttctgggg gaggatgtac gtggccatgt atgaagccaa atattaggct t aaaaactga    2063 aaaatctggt tcattcttca gatatactgg aacccttttta aagttgatat t ggggccatg    2123 agtaaaatag attttataag atgactgtgt tgtaccaaaa ttcatctgtc t atattttat    2183 ttaggggaac atggtttgac tcatcttata tgggaaacca tgtagcagtg a gtcatatct    2243 taatatattt ctaaatgttt ggcatgtaaa tgtaaactca gcatcaaaat a tt           2296
```

<210> SEQ ID NO 4
<211> LENGTH: 358
<212> TYPE: PRT
<213> ORGANISM: Homo sapiens

<400> SEQUENCE: 4

```
Met Gly Asn Ala Ser Asn Asp Ser Gln Ser Glu Asp Cys Glu Thr Arg
 1               5                  10                  15

Gln Trp Leu Pro Pro Gly Glu Ser Pro Ala Ile Ser Ser Val Met Phe
            20                  25                  30

Ser Ala Gly Val Leu Gly Asn Leu Ile Ala Leu Ala Leu Leu Ala Arg
        35                  40                  45

Arg Trp Arg Gly Asp Val Gly Cys Ser Ala Gly Arg Arg Ser Ser Leu
    50                  55                  60

Ser Leu Phe His Val Leu Val Thr Glu Leu Val Phe Thr Asp Leu Leu
65                  70                  75                  80

Gly Thr Cys Leu Ile Ser Pro Val Val Leu Ala Ser Tyr Ala Arg Asn
                85                  90                  95

Gln Thr Leu Val Ala Leu Ala Pro Glu Ser Arg Ala Cys Thr Tyr Phe
            100                 105                 110

Ala Phe Ala Met Thr Phe Phe Ser Leu Ala Thr Met Leu Met Leu Phe
        115                 120                 125

Ala Met Ala Leu Glu Arg Tyr Leu Ser Ile Gly His Pro Tyr Phe Tyr
    130                 135                 140

Gln Arg Arg Val Ser Arg Ser Gly Gly Leu Ala Val Leu Pro Val Ile
145                 150                 155                 160

Tyr Ala Val Ser Leu Leu Phe Cys Ser Leu Pro Leu Leu Asp Tyr Gly
                165                 170                 175

Gln Tyr Val Gln Tyr Cys Pro Gly Thr Trp Cys Phe Ile Arg His Gly
            180                 185                 190

Arg Thr Ala Tyr Leu Gln Leu Tyr Ala Thr Leu Leu Leu Leu Leu Ile
        195                 200                 205

Val Ser Val Leu Ala Cys Asn Phe Ser Val Ile Leu Asn Leu Ile Arg
    210                 215                 220

Met His Arg Arg Ser Arg Arg Ser Arg Cys Gly Pro Ser Leu Gly Ser
225                 230                 235                 240

Gly Arg Gly Gly Pro Gly Ala Arg Arg Gly Glu Arg Val Ser Met
                245                 250                 255

Ala Glu Glu Thr Asp His Leu Ile Leu Leu Ala Ile Met Thr Ile Thr
            260                 265                 270
```

Phe Ala Val Cys Ser Leu Pro Phe Thr Ile Phe Ala Tyr Met Asn Glu
            275                 280                 285

Thr Ser Ser Arg Lys Glu Lys Trp Asp Leu Gln Ala Leu Arg Phe Leu
        290                 295                 300

Ser Ile Asn Ser Ile Ile Asp Pro Trp Val Phe Ala Ile Leu Arg Pro
305                 310                 315                 320

Pro Val Leu Arg Leu Met Arg Ser Val Leu Cys Cys Arg Ile Ser Leu
                325                 330                 335

Arg Thr Gln Asp Ala Thr Gln Thr Ser Cys Ser Thr Gln Ser Asp Ala
            340                 345                 350

Ser Lys Gln Ala Asp Leu
        355

<210> SEQ ID NO 5
<211> LENGTH: 39
<212> TYPE: DNA
<213> ORGANISM: Homo sapiens

<400> SEQUENCE: 5
gatgagctct ttaaaaggag ggcgcatctc ttttccagg                         39

<210> SEQ ID NO 6
<211> LENGTH: 18
<212> TYPE: DNA
<213> ORGANISM: Homo sapiens

<400> SEQUENCE: 6
ggtgaacacc agctcggt                                                18

<210> SEQ ID NO 7
<211> LENGTH: 18
<212> TYPE: DNA
<213> ORGANISM: Homo sapiens

<400> SEQUENCE: 7
cttacctgca gctgtacg                                                18

<210> SEQ ID NO 8
<211> LENGTH: 18
<212> TYPE: DNA
<213> ORGANISM: Homo sapiens

<400> SEQUENCE: 8
gatggcaaag acccaagg                                                18

<210> SEQ ID NO 9
<211> LENGTH: 32
<212> TYPE: DNA
<213> ORGANISM: Homo sapiens

<400> SEQUENCE: 9
atctggcacc acaccttcta caagtagctg cg                                32

<210> SEQ ID NO 10
<211> LENGTH: 32
<212> TYPE: DNA
<213> ORGANISM: Homo sapiens

<400> SEQUENCE: 10
cgtcatactc ctgcttgctg atccacatct gc                                32